US008939907B2

(12) United States Patent
Koest

(10) Patent No.: US 8,939,907 B2
(45) Date of Patent: Jan. 27, 2015

(54) OPHTHALMIC ANALYSIS SYSTEM FOR MEASURING THE INTRAOCULAR PRESSURE IN THE EYE

(75) Inventor: Gert Koest, Hannover (DE)

(73) Assignee: Oculus Optikgeraete GmbH, Wetzlar Dutenhofen (DE)

( * ) Notice: Subject to any disclaimer, the term of this patent is extended or adjusted under 35 U.S.C. 154(b) by 0 days.

(21) Appl. No.: 13/231,907

(22) Filed: Sep. 13, 2011

(65) Prior Publication Data

US 2012/0065488 A1    Mar. 15, 2012

Related U.S. Application Data

(62) Division of application No. 11/351,678, filed on Feb. 10, 2006, now abandoned.

(30) Foreign Application Priority Data

Feb. 16, 2005   (DE) ................. 20 2005 002 562 U

(51) Int. Cl.
  *A61B 3/16*   (2006.01)
  *A61B 3/10*   (2006.01)
  *A61B 3/107*  (2006.01)

(52) U.S. Cl.
  CPC ............. *A61B 3/165* (2013.01); *A61B 3/1005* (2013.01); *A61B 3/107* (2013.01)
  USPC ......................................... 600/401; 600/405

(58) Field of Classification Search
  CPC ....................................................... A61B 3/165
  USPC ............................ 600/398–405; 351/205–221
  See application file for complete search history.

(56) References Cited

U.S. PATENT DOCUMENTS

| 4,440,477 | A |   | 4/1984  | Schachar |
| 4,523,821 | A |   | 6/1985  | Lang et al. |
| 4,825,873 | A | * | 5/1989  | Kohayakawa ............... 600/401 |
| 4,947,849 | A | * | 8/1990  | Takahashi et al. .......... 600/401 |
| 5,002,056 | A |   | 3/1991  | Takahashi et al. |
| 5,299,573 | A | * | 4/1994  | Kobayashi ................... 600/401 |
| 5,404,884 | A |   | 4/1995  | Lempert |
| 5,474,066 | A | * | 12/1995 | Grolman ..................... 600/398 |
| 5,512,965 | A | * | 4/1996  | Snook ........................ 351/205 |
| 5,523,808 | A |   | 6/1996  | Kohayakawa |

(Continued)

FOREIGN PATENT DOCUMENTS

WO    WO 03/096888 A1   11/2003

OTHER PUBLICATIONS

"CCD Image Sensors and Analog-to-Digital Conversion." Texas Instruments. Jan. 1993. Pages: Title p. 10.*

(Continued)

*Primary Examiner* — Max Hindenburg
*Assistant Examiner* — John Pani
(74) *Attorney, Agent, or Firm* — Blakely, Sokoloff, Taylor & Zafman LLP

(57) ABSTRACT

The invention relates to an ophthalmic analysis system for measuring the intraocular pressure in an eye comprising an actuating device for contact-free deformation of the cornea, an observation system with which the deformation of the cornea can be observed and recorded, an analysis device with which the intraocular pressure can be deduced from the image information of the observation system, wherein split images of at least parts of the undeformed and/or deformed cornea can be recorded using the observation system.

2 Claims, 2 Drawing Sheets

(56) References Cited

U.S. PATENT DOCUMENTS

| | | | | |
|---|---|---|---|---|
| 6,053,867 A | * | 4/2000 | Iijima | 600/399 |
| 6,091,999 A | * | 7/2000 | Crump et al. | 700/112 |
| 6,120,444 A | | 9/2000 | Miyakawa et al. | |
| 2003/0187342 A1 | | 10/2003 | Cuzzani et al. | |
| 2004/0183998 A1 | * | 9/2004 | Luce | 351/212 |
| 2004/0207811 A1 | | 10/2004 | Elsner | |
| 2004/0260168 A1 | | 12/2004 | Shimmyo | |
| 2011/0118585 A1 | * | 5/2011 | Ishii et al. | 600/401 |

OTHER PUBLICATIONS

European Patent Office Search Report for Counterpart EPO Patent Application No. EP 05028292.0-2305, 7 pages, Jun. 20, 2006.

* cited by examiner

OPHTHALMIC ANALYSIS SYSTEM FOR MEASURING THE INTRAOCULAR PRESSURE IN THE EYE

CROSS-REFERENCE TO RELATED APPLICATIONS

This application is a divisional of application Ser. No. 11/351,678, filed Feb. 10, 2006 now abandoned, which claims the benefit of German Application No. 20 2005 002 562.3, filed Feb. 16, 2005.

FIELD

The invention relates to an ophthalmic analysis system for measuring the intraocular pressure in the eye (eye internal pressure) according to the preamble of claim 1.

BACKGROUND

Serious health impairments can be triggered by an elevated intraocular pressure. In particular, the optic nerve can be damaged by the elevated intraocular pressure which causes so-called glaucoma with restrictions of the visual field.

Three basic principles are known for checking the intraocular pressure, namely impression tonometry, applanation tonometry and noncontact tonometry. The impression tonometer measures the depth of the indentability of the cornea caused by a metal stamp loaded with a known weight. For the same weight the indentability is inversely proportional to the intraocular pressure, that is the indentability is greater, the lower is the intraocular pressure and conversely. A disadvantage with impression tonometry is that the placement of the tonometer and the impression of the metal stamp additionally increase the intraocular pressure so that the measured pressure does not correspond exactly to the actual intraocular pressure. Furthermore, the placement of the stamp on the cornea of the patient's eye is relatively stressful for the patients.

Furthermore, so-called applanation tonometers are also known for measuring the intraocular pressure, its measurement being based on application of the applanation principle. The applanation principle starts from Ingbert's law which states that the pressure in a spherical container filled with liquid corresponds to the counterpressure which flattens a certain surface of this sphere. The intraocular pressure can be measured on the basis of this law in two different ways. According to a first alternative, a tonometer with constant weight can be used and the flattened surface can be measured. According to an alternative method of measurement, the force required to flatten a known surface of constant size is used A Perkins applanation tonometer is known, which consists of a plastic cylinder whose lower planar end is provided with a gradation. A magnifying glass is located at the upper end. After instilling a fluorescent liquid into the conjunctival sac, the diameter of the applanated corneal surface can be determined by optical reading off on the gradation scale. In this case, the intraocular pressure is determined by means of a constant force.

In addition, an applanation tonometer operating on the principle of an applanated surface of constant size is known. In this case, the cornea is flattened using the quadrilateral base of a glass prism. The intraocular pressure is measured by intensifying the pressure of the prism on the eye until the flattened circular region of the cornea is at the same level as the four sides of the prism base. A disadvantage with applanation tonometers again is that as a result of the deformation of the cornea by means of an actuating element, considerable stress is produced for the patients.

So-called noncontact tonometers were developed to avoid this stressing produced by contact with a deforming tool. In these noncontact tonometers actuating devices are provided for deforming the cornea with which the cornea is deformed free from contact. For this purpose, a puff of compressed air is produced for example and directed onto the cornea. In known noncontact tonometers air puffs are directed onto the eye in the direction of the optic axis whereby the cornea is increasingly flattened and finally indented. To measure the deformation of the cornea, an obliquely incident bundle of parallel light rays is directed onto the cornea and the light reflected by the cornea is measured as a measurement signal. For this purpose, the reflected light can be intercepted by a light sensor, for example, where the light intensity measured by the light sensor varies as a function of the applanation of the cornea caused by the air flow.

A disadvantage in all known methods of measurement is that when measuring the intraocular pressure, the counterpressure caused by the elastic deformation of the cornea is not taken into account. This is because the cornea itself is stretched over the vitreous body in the fashion of an elastic membrane so that during the measurement of the intraocular pressure a certain amount of force is required for its deformation which is included in the measurement results in a falsifying manner. This falsification is of a different magnitude in different patients since the properties of the cornea, especially its thickness and elasticity, vary within certain limits.

SUMMARY

Starting from this prior art, it is thus the object of the present invention to propose a new ophthalmic analysis system for measuring the intraocular pressure which avoids the disadvantages of the previously known prior art.

This object is solved by an analysis system according to the teaching of claim 1.

Advantageous embodiments of the invention are the subject matter of the dependent claims.

The analysis system according to the invention is based on the basic idea of recording split images of the cornea before and/or during and/or after the deformation of the cornea, which show the state of the cornea in a plane of intersection. These split images are analyzed in the analysis device by means of suitable image processing methods and provide additional information on the state of the cornea which can be taken into account when deducing the intraocular pressure.

The thickness of the cornea has a major influence on the measured values and thus on the result of measurement of the intraocular pressure since the cornea as an elastically deformable membrane opposes the deformation force applied by the actuating device with a counterforce which does not depend on the intraocular pressure itself and can therefore falsify the measurement of the intraocular pressure. It is thus particularly advantageous if the thickness of the cornea is deduced from split images of the cornea. Taking into account the known elasticity characteristics of the cornea, the counterforce applied by the cornea during the elastic deformation can be estimated from the thickness of the cornea and taken into account as an influential factor when deducing the intraocular pressure.

Alternatively or additionally to determining the thickness of the cornea as an influential factor, the curvature of the cornea can also be derived from the split images of the cornea.

The curvature of the cornea also influences the measurement results and should thus be taken into account when deducing the intraocular pressure.

In addition, it is also possible to determine the light scattering of the cornea from the split images of the cornea. The light scattering of the cornea has a specific relationship to the elasticity characteristic of the cornea so that the elasticity of the cornea can be deduced from the light scattering.

It is fundamentally arbitrary which method of measurement is used to measure the intraocular pressure itself and for the derivation in the analysis system. For example, the known reflected light methods can be used for this purpose, where the split images recorded according to the invention are then used, for example, merely to correct for the influence produced by the elastic deformation of the cornea. However, it is especially advantageous if the intraocular pressure is also deduced from the split image recordings of the deformed cornea. These split image recordings represent the deformation of the cornea caused by the actuating device extraordinarily exactly and thus contain the image information required to deduce the intraocular pressure. For example, during the deformation of the cornea a plurality of split images can be recorded successively as a series of images so that the split image with the greatest deformation of the cornea can then be extracted in the following image analysis. The intraocular pressure can then simply be derived from this image of the cornea with the greatest deformation taking into account the thickness of the cornea.

The equipment used to obtain the split image recordings of the cornea is fundamentally arbitrary. It is especially advantageous if the observation system comprises a slit projector which can project a light slit onto the cornea. Slit projectors of this type are known from ophthalmology. The necessary illumination principle of the slit projector is based on the fact that the refractive media of the ocular anterior chamber are not transparent but significant scattering takes place at said media, especially in the short-wavelength fraction of the visible light. This has the result that a focused light beam, that is in the present case the projected light slit which is passed through the optical media of the eye, makes the ocular structures and in particular the cornea visible as a split image when viewed laterally since the light is scattered at different intensities on passage through the different materials, especially on passage through the cornea. The slit-shaped light beam thereby produces an image plane which runs through the ocular body in cross section so that the split images to be recorded using the observation system lie specifically in this image plane defined by the light slit.

In order to he able to record the split images illuminated by the light slit, the observation system should comprise a recording device which is arranged so that the image plane illuminated by the slit projector can be recorded at least partly.

In order to enhance the image quality, at least one objective, that is a lens arrangement can be arranged between cornea and recording device. Using this lens arrangement the image plane of the cornea illuminated by the slit projector is imaged on a recording plane in the recording device.

In order to achieve a large depth of focus in the split images, the arrangement of the image plane in the cornea illuminated by the slit projector, the principal plane of the lens system between the cornea and the recording device (objective plane) and the recording plane of the recording device should satisfy the Scheimpflug condition. This rule developed from the photographs of Scheimpflug prescribes that the image plane, the objective plane and the recording plane are arranged at angles such that they intersect in a common axis. By tilting the recording plane relative to the object plane, the image plane can be brought into an arbitrary spatial position wherein image points are detected in the depth of focus which cannot otherwise be sharply imaged at the same time when the image plane is perpendicular.

For contact-free deformation of the cornea it is particularly advantageous if a flow pulse of a gaseous medium, especially air, can be applied to the surface of the cornea using the actuating device. The stressing of the patients through such an air jet is relatively very small and is not perceived as very stressful because of its shortness.

The actuating device can be constructed by providing a pressure chamber with a nozzle orifice directed onto the eye to be examined. As a result of a short-term increase in the pressure in the pressure chamber, the gas located in the pressure chamber flows out through the nozzle orifice and in this way forms the desired flow pulse on the surface of the eye. The increase in the pressure in the pressure chamber can be achieved for example, by moving a mechanically driven stamp in a cylindrical opening of the pressure chamber.

In order that the deformation of the cornea can be correlated with the strength of the flow pulse, a sensor, for example, a pressure sensor should be provided in or on the pressure chamber which can be used to measure the intensity of the flow pulse directly or indirectly. If, for example, the increase in the internal pressure in the pressure chamber is measured using a pressure sensor, the intensity of the flow pulse can be deduced directly from this pressure profile if the diameter of the nozzle orifice is known. This measured value can then likewise be passed to the analysis device and be taken into account there in calculations of the other measured parameters.

In order to allow the corneal deformation to be measured as accurately as possible, the ray path of the slit projector should run coaxially to the longitudinal axis of the flow pulse when impinging upon the cornea.

This can be achieved in particular by the ray path of the slit projector running through the actuating device.

At the points of passage of the ray path through the actuating device, either recesses such as one formed in particular by the nozzle orifice or transparent materials should be provided, through which the light from the slit projector can pass.

Alternatively thereto, deflecting optics can also be provided whereby the ray path of the slit projector is guided past the actuating device and the nozzle orifice.

Which type of recording device is used to record the split images is fundamentally arbitrary. It is especially advantageous if this is a high-speed recording device with which split images can be recorded in a rapid image sequence so that a plurality of split images can be recorded during the deformation of the cornea. By analyzing this image sequence which shows the cornea from the beginning of deformation via the point of maximum deformation until the end of deformation, the desired measurement parameters can be derived very exactly.

It is particularly preferable if a video sensor is provided as recording device which reproduces the image data of the split images in the form of a video signal. The video signal should preferably be produced in digital form or be converted from an analog format into a digital format since digital video signals in known data processing systems can be analyzed very well by known image processing systems.

In particular, CCD chips or CMOS chips can be used as video sensors since these make it possible to achieve high-resolution recordings and at the same time are available cost-effectively. The split images of the cornea according to the invention need not necessarily involve frames wherein the recorded section of the cornea is entirely shown pictorially. Rather, line scan cameras or a plurality of adjacently arranged line scan cameras can also be used as video sensors. The line scan cameras should be arranged in the recording plane such that the image of the cornea is imaged on the line scan camera such that any deformation of the cornea can be identified by the line scan camera.

Alternatively to using line scan cameras, area scan cameras, for example area scan CCD chips or CMOS chips can naturally also be used as video sensors.

In order to simplify the alignment of the eye to be examined on the analysis system for the treating physician, the analysis system can have an adjusting camera.

BRIEF DESCRIPTION OF THE DRAWINGS

One embodiment of the invention is shown schematically in the drawings and is explained as an example hereinafter.

In the drawings.

DETAILED DESCRIPTION

Figure 1:
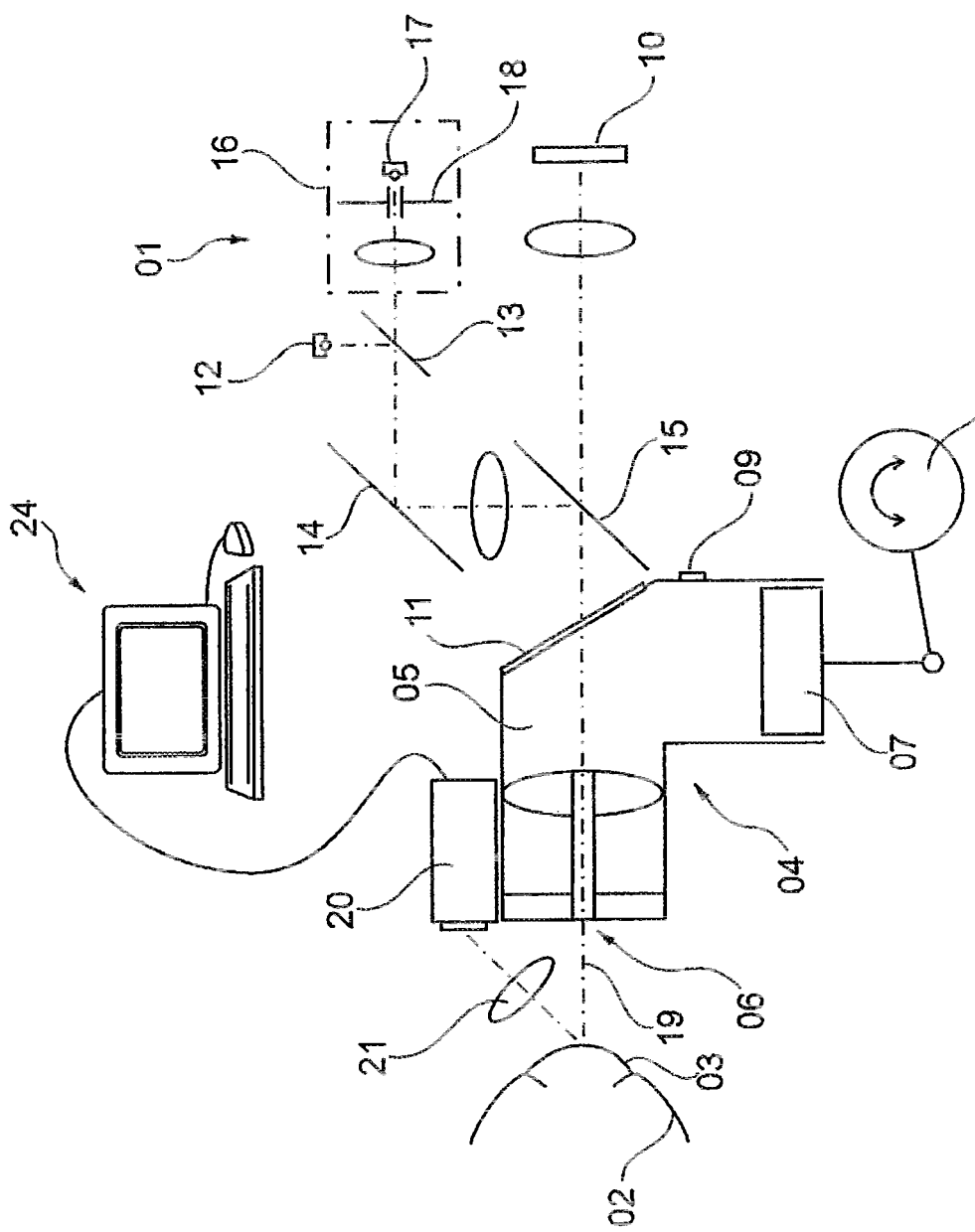
FIG. 1: shows the structure of an analysis system according to the invention for measuring the intraocular pressure.

The analysis system 01 shown schematically in FIG. 1 is used to examine an eye 02 which is shown schematically. In particular, the intraocular pressure of the eye 02 and the thickness of the cornea 03 can be measured using the analysis system 01.

In order to be able to determine the intraocular pressure of the eye 02, the cornea 03 must be slightly deformed. An actuating device 04 is used for this purpose. The actuating device 04 comprises a closed pressure chamber 05 which has a nozzle orifice 06 on its side pointing towards the eye 02. A piston 07 which can be moved up and down by driving a drive shaft 08 in the pressure chamber 05 is used to increase the internal pressure in the pressure chamber 05. If the piston 07 is moved into the interior of the pressure chamber 05 with a rapid adjusting movement, the air in the pressure chamber 05 is expelled outwards through the nozzle orifice 06 and thereby produces a flow pulse which impinges on the cornea 03 and deforms this without contact. In order to be able to measure the intensity of the pressure pulse, a pressure sensor 09 is provided at the pressure chamber 05 which can measure the increase in the internal pressure in the pressure chamber 05. The intensity of the flow pulse impinging on the cornea 03 through the nozzle orifice 06 can be derived from these pressure values.

An adjusting camera 10 is used to be able to align the eye 02 in the exact position with respect to the analysis device 01. The adjusting camera 10 can be used to aim at the eye 02 through a transparent cover 11 of the pressure chamber 05 and through the nozzle orifice 06 so that the treating physician can assess the correct alignment position of the eye 02 with respect to the analysis device 01. In order to be able to fix the eye 02 in the desired position during the examination, a fixing light 12 is provided whose visible light is guided by means of the mirrors 13, 14 and 15 onto the eye 02 by the actuating device 04. The mirrors 13 and 15 are constructed as semi-transparent.

Further provided in the analysis system 01 is a slit projector 16 which can be used to project a light slit onto the cornea 03. In the slit projector 16 the light is produced by means of a lamp 17 and is formed into a light slit by means of a collimating slit 18. In this case, xenon high-pressure lamps or suitable light-emitting diodes can be used as lamps in the slit projector 16.

The light slit produced in the slit projector 16 is used to illuminate the eye 02 in a plane of intersection which runs along the principal optic axis 19 perpendicular to the image plane of FIG. 1. Split images of this type are shown schematically in FIG. 2 to FIG. 4.

A recording device 20 which can be used to observe the planes of intersection illuminated by the light slit at an angle is used for observation and recording before, during and after the deformation. An objective 21 is positioned between the recording device 20 and the eye 02 such that Scheimpflug recordings can be made of the planes of intersection of the cornea illuminated by the light beam. In the recording device 20 a CCD chip or CMOS chip is used as the video sensor whose image data is transferred to an analysis device 24 which is installed as software on an industry standard PC.

Figure 2:
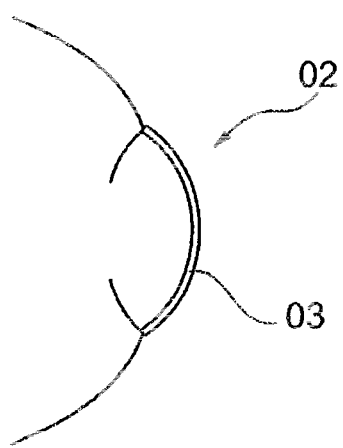
FIG. 2: shows the split image plane of an eye with nondeformed cornea shown schematically.
Figure 3:
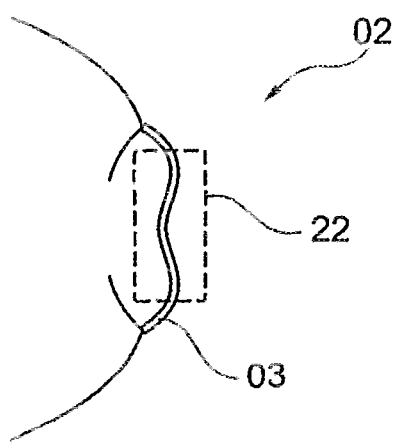
FIG. 3: shows the split image plane of the eye from FIG. 2 with deformed cornea and arrangement of the image area of an area scan camera.
Figure 4:
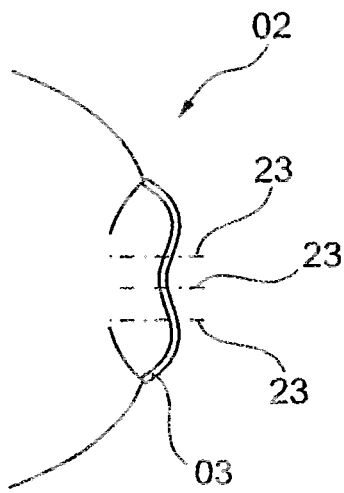
FIG. 4: shows the split image plane from FIG. 2 with deformed cornea and arrangement of the image area comprising several line scan cameras.

FIGS. 2 to 3 are schematic diagrams showing the eye 02 in the split image plane illuminated by the slit projector 16. FIG. 2 shows the eye 02 with undeformed cornea 03. The thickness of the cornea 03 can be deduced by image data processing of the images recorded using the recording device 20 and taken into account in the calculation of the intraocular pressure.

FIG. 3 shows the area bordered by a dashed line which can be recorded using the CCD or CMOS video sensor built into the recording device 20. The image zone comprises a rectangular area which comprises the cornea 03 at its center. During the deformation of the cornea 03, a plurality of split images are recorded using the recording device and then the intraocular pressure is deduced by image data processing from the image sequence of the deformed cornea 03 taking into account the thickness of the cornea 03 and the measurement data of the pressure sensor 09.

Alternatively to an area scan camera, one or a plurality of line scan cameras can be used in the recording device 20. The image zone 23 of these line scan cameras is shown schematically in FIG. 4.

What is claimed is:

1. An ophthalmic analysis system to measure an intraocular pressure in an eye, comprising:
    an actuating device including a pressure chamber, the actuating device to expel a flow pulse of a gaseous medium in response to an increase in internal pressure within the pressure chamber, wherein the actuating device includes an at least partially transparent cover of the pressure chamber and a nozzle orifice to direct the flow pulse onto the eye, when the eye is positioned in front of the nozzle orifice, thereby deforming a cornea of the eye;
    an observation system comprising a high-speed recording device including a CCD or CMOS video sensor, the observation system to observe and record a consecutive series of split images of an image plane, and, when the eye is positioned in front of the nozzle orifice, of at least parts of the cornea while undeformed and while deformed by the actuating device, wherein the video sensor reproduces corresponding split image data;
    first, second, and third mirrors, wherein the first and second mirrors are semi-transparent;

an adjusting camera to enable alignment of the eye with respect to the ophthalmic analysis system, wherein the adjusting camera is aimed through the first mirror, the transparent cover, and the nozzle orifice coaxially to the longitudinal axis of the flow pulse of the gaseous medium;

a slit projector to project a light slit in front of the nozzle orifice and, when the eye is positioned in front of the nozzle orifice, onto the cornea, wherein a ray path of the light slit produced by the slit projector initially runs parallel to the aim of the adjusting camera and through the second mirror before reflecting off of the third and first mirrors and passing through the transparent cover and the nozzle orifice coaxially to the longitudinal axis of the flow pulse of the gaseous medium, wherein the slit projector illuminates the image plane and wherein the split images recorded with the observation system lie in the image plane illuminated by the slit projector;

a fixing light to enable alignment of the eye with respect to the ophthalmic analysis system, wherein a ray path of a light beam produced by the fixing light reflects off of the first, second, and third mirrors and passes through the transparent cover and the nozzle orifice coaxially to the longitudinal axis of the flow pulse of the gaseous medium;

an objective arranged in an objective plane between the image plane illuminated by the slit projector and the observation system, wherein the image plane, a plane of the objective, and a recording plane are arranged such that the image plane is imaged according to the Scheimpflug condition on the recording plane of the observation system; and a pressure sensor to measure an intensity of the flow pulse, wherein the observation system is configured to transfer the split images of the cornea to a computer, wherein the split images include a plurality of images of the cornea while deformed by the actuating device wherein the plurality of images include split images in which a portion of the cornea is convex while the cornea is undeformed and concave during a greatest deformation of the cornea.

2. The ophthalmic analysis system of claim 1, further comprising:

the computer, wherein the computer is configured to extract a split image with the greatest deformation of the cornea.

* * * * *